(12) United States Patent
Hataminia et al.

(10) Patent No.: US 10,626,068 B2
(45) Date of Patent: Apr. 21, 2020

(54) SQUALENE EXTRACTION FROM SEED OILS

(71) Applicants: Fatemeh Hataminia, Mashhad (IR); Nafiseh Farhadian, Mashhad (IR); Mahmoud Ebrahimi, Mashhad (IR)

(72) Inventors: Fatemeh Hataminia, Mashhad (IR); Nafiseh Farhadian, Mashhad (IR); Mahmoud Ebrahimi, Mashhad (IR)

( * ) Notice: Subject to any disclaimer, the term of this patent is extended or adjusted under 35 U.S.C. 154(b) by 56 days.

(21) Appl. No.: 16/136,204

(22) Filed: Sep. 19, 2018

(65) Prior Publication Data
US 2019/0016651 A1    Jan. 17, 2019

Related U.S. Application Data

(60) Provisional application No. 62/560,208, filed on Sep. 19, 2017.

(51) Int. Cl.
*C07C 7/148*    (2006.01)
*C07C 11/21*   (2006.01)
(Continued)

(52) U.S. Cl.
CPC ............ *C07C 7/1485* (2013.01); *C01G 49/02* (2013.01); *C01G 49/08* (2013.01); *C07C 1/207* (2013.01); *C07C 11/21* (2013.01); *C09C 1/24* (2013.01); *C11C 1/025* (2013.01); *C11C 1/08* (2013.01); *C01P 2002/82* (2013.01); *C01P 2004/04* (2013.01); *C01P 2004/64* (2013.01); *C01P 2006/42* (2013.01)

(58) Field of Classification Search
None
See application file for complete search history.

(56) References Cited

U.S. PATENT DOCUMENTS

| | | | | |
|---|---|---|---|---|
| 2005/0250953 A1* | 11/2005 | May | ...................... | C07D 311/72 549/413 |
| 2014/0155670 A1* | 6/2014 | Slowing | .................... | C07C 1/22 585/733 |
| 2015/0298993 A1* | 10/2015 | Lead | .................. | B01J 20/28009 210/663 |

FOREIGN PATENT DOCUMENTS

FR        3043553 A1 *  5/2017  ............. A61K 31/55

OTHER PUBLICATIONS

Machine translation FR 3043553 May 19, 2017. translation dated Dec. 20, 2019 (Year: 2019).*

* cited by examiner

*Primary Examiner* — In Suk C Bullock
*Assistant Examiner* — Alyssa L Cepluch
(74) *Attorney, Agent, or Firm* — Bajwa IP Law Firm; Haris Zaheer Bajwa

(57) ABSTRACT

A method for squalene extraction from a seed oil includes converting fatty acids of the seed oil into soap by subjecting the seed oil to a saponification reaction to obtain a saponified product, and adsorbing the fatty acids of the seed oil on surfaces of iron oxide nanoparticles to obtain iron oxide nanoparticles coated with fatty acids. The method may further include washing the iron oxide nanoparticles coated with fatty acids with a polar solvent to obtain a third mixture including a polar phase and the iron oxide nanoparticles coated with fatty acids, separating the iron oxide nanoparticles coated with fatty acids from the third mixture by a magnetic field, mixing the polar phase with a non-polar solvent and distilled water to obtain a two-phase solution, the two-phase solution including a non-polar phase and an aqueous phase, and separating and drying the non-polar phase to obtain squalene.

10 Claims, 9 Drawing Sheets

(51) Int. Cl.
*C07C 1/207* (2006.01)
*C11C 1/08* (2006.01)
*C01G 49/02* (2006.01)
*C11C 1/02* (2006.01)
*C01G 49/08* (2006.01)
*C09C 1/24* (2006.01)

SQUALENE EXTRACTION FROM SEED OILS

CROSS-REFERENCE TO RELATED APPLICATION

This application claims the benefit of priority from U.S. Provisional Patent Application Ser. No. 62/560,208, filed on Sep. 19, 2017, and entitled "SQUALENE EXTRACTION FROM PUMPKIN SEED OIL BY EVALUATION OF ITS ANTI-ANGIOGENESIS IMPACT," which is incorporated herein by reference in its entirety.

TECHNICAL FIELD

The present disclosure generally relates to squalene extraction from seed oils, for example for applications thereof as an anti-angiogenesis agent.

BACKGROUND

Squalene is an unsaturated organic compound, which plays a role in synthesis of cholesterol, steroid hormone, and vitamin D and E in human body. Squalene may also be used in the treatment of various cancers. Squalene resources include animals and natural oils. Extracted squalene from animals, for example, the squalene extracted from shark liver oil, is expensive. The squalene synthesized by biochemical synthesis methods are in a coiled and sterol-like form, while only the linear form of squalene is metabolized in the human body. Therefore, extracting squalene from vegetable seed oils, such as pumpkin, olive, and soybean seed oils, allows for non-expensive and safe extraction of the squalene.

Considering the complexity of methods for extracting squalene from natural oils that involve utilizing super critical fluids, chromatography or distillation in vacuum, there is a need for new extraction methods for extracting squalene from natural oils.

SUMMARY

In one general aspect, the present disclosure is directed to a method for squalene extraction from a seed oil. The method may include converting fatty acids of the seed oil into soap by subjecting the seed oil to a saponification reaction to obtain a saponified product, adsorbing the fatty acids of the seed oil on surfaces of iron oxide nanoparticles to obtain iron oxide nanoparticles coated with fatty acids by dissolving the saponified product in water to obtain an aqueous solution, mixing iron oxide nanoparticles with the aqueous solution to obtain a first mixture, and heating the first mixture.

According to an implementation, the saponification reaction may include mixing the seed oil with an ethanolic KOH solution to obtain a second mixture, and heating the second mixture under reflux. According to another implementation, heating the second mixture under reflux may include heating the second mixture at a temperature of between 70° C. and 80° C.

According to an implementation, dissolving the saponified product in water to obtain an aqueous solution may include obtaining an aqueous solution with a concentration of between 0.023 mmol/mL and 0.34 mmol/mL.

According to one or more implementations, heating the first mixture may include heating the first mixture at a temperature of between 100° C. and 195° C. According to an implementation, heating the first mixture at a temperature of between 100° C. and 195° C. may be carried out for 30 min to 6.5 hours.

According to some implementations, mixing iron oxide nanoparticles with the aqueous solution to obtain a first mixture may include mixing iron oxide nanoparticles with the aqueous solution with a molar ratio of (aqueous solution to iron oxide nanoparticles) between 0.3 mol/mol and 1.9 mol/mol.

According to some implementations, the disclosed method may further include washing the iron oxide nanoparticles coated with fatty acids with a polar solvent to obtain a third mixture, the third mixture including a polar phase and the iron oxide nanoparticles coated with fatty acids, separating the iron oxide nanoparticles coated with fatty acids from the third mixture using a magnetic field, mixing the polar phase with a non-polar solvent and distilled water to obtain a two-phase solution, the two-phase solution including a non-polar phase and an aqueous phase, separating the non-polar phase, and drying the separated non-polar phase to obtain squalene. According to an implementation, the polar solvent may be acetone and the organic solvent may be hexane.

According to an implementation, mixing the second remaining solution with an organic solvent and distilled water to obtain a two-phase solution may be carried out at a temperature of between 10° C. and 40° C.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

The following describes techniques and methods for squalene extraction from a seed oil, such as pumpkin seed oil, by first saponifying the fatty acids of the seed oil and then utilizing magnetic nanoparticles to adsorb the fatty acids and separate them from the seed oil and then extract squalene from the remaining unsaponified components by a solvent extraction method.

Figure 1:
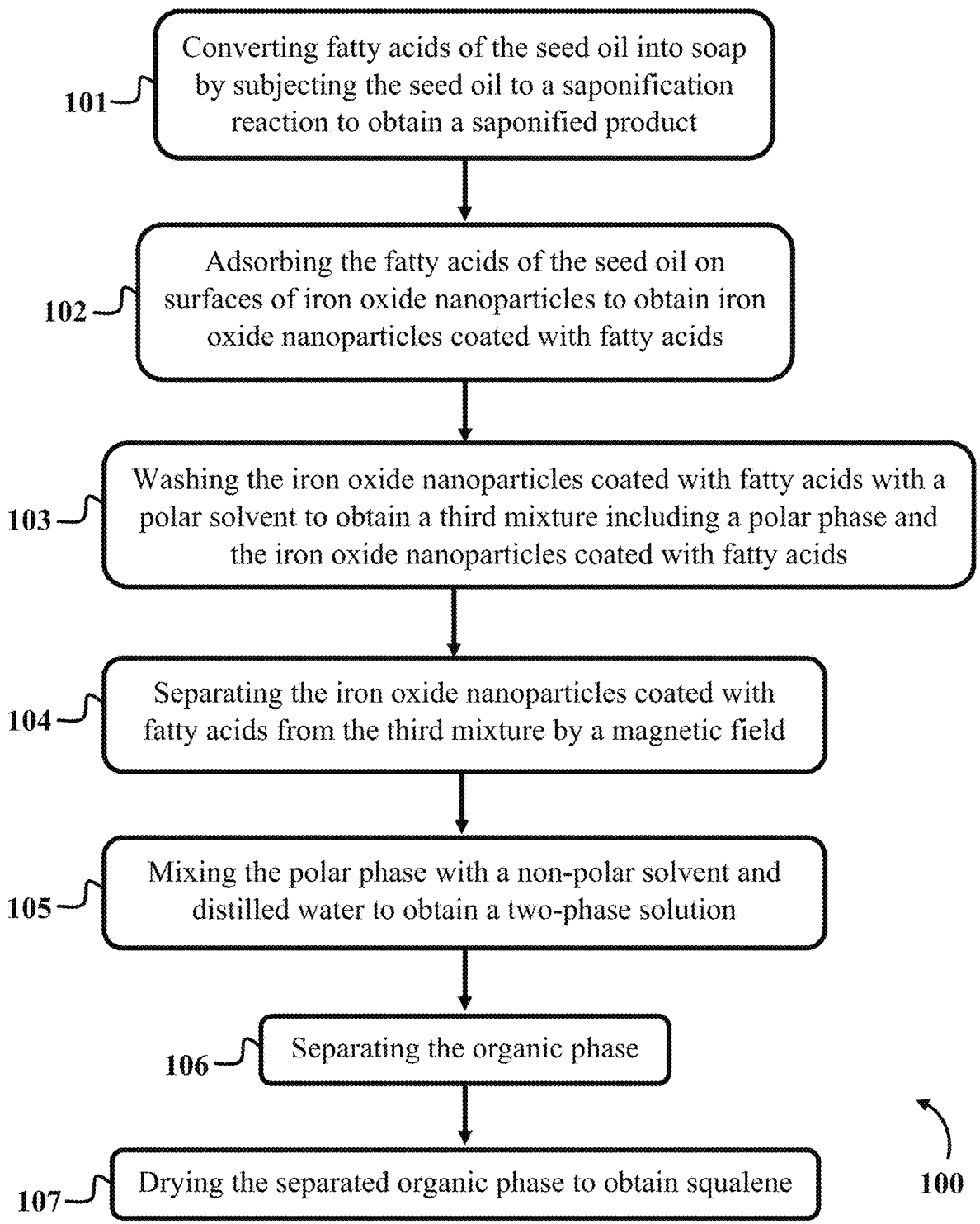
FIG. 1 illustrates an implementation of a method for squalene extraction from a seed oil.

FIG. 1 illustrates an implementation of a method 100 for squalene extraction from a seed oil, such as pumpkin seed oil. The method 100 may include a step 101 of converting fatty acids of the seed oil into soap by subjecting the seed oil to a saponification reaction to obtain a saponified product; a step 102 of adsorbing the fatty acids of the seed oil on surfaces of iron oxide nanoparticles to obtain iron oxide nanoparticles coated with fatty acids; a step 103 of washing the iron oxide nanoparticles coated with fatty acids with a polar solvent to obtain a third mixture, the third mixture including a polar phase and the iron oxide nanoparticles coated with fatty acids; a step 104 of separating the iron oxide nanoparticles coated with fatty acids from the third mixture by a magnet; a step 105 of mixing the polar phase with an organic solvent and distilled water to obtain a two-phase solution; a step 106 of separating the organic phase; and a step 107 of drying the separated organic phase to obtain squalene.

Referring to FIG. 1, according to one or more implementations, in the step 101 of converting fatty acids of the seed oil into soap by subjecting the seed oil to a saponification reaction to obtain a saponified product, the saponification reaction may include mixing the seed oil with an ethanolic KOH solution to obtain a second mixture, and then heating the second mixture under reflux. According to an implementation, the second mixture may be obtained by mixing the seed oil with the ethanolic potassium hydroxide (KOH) solution. Esters, triglycerides, and free fatty acids of the seed oil react with KOH and convert to soap. According to an implementation, heating the second mixture under reflux may include heating the second mixture at a temperature of approximately 70° C. to approximately 80° C. in order to fully dry the saponified product by removing the ethanol solvent.

Figure 2:
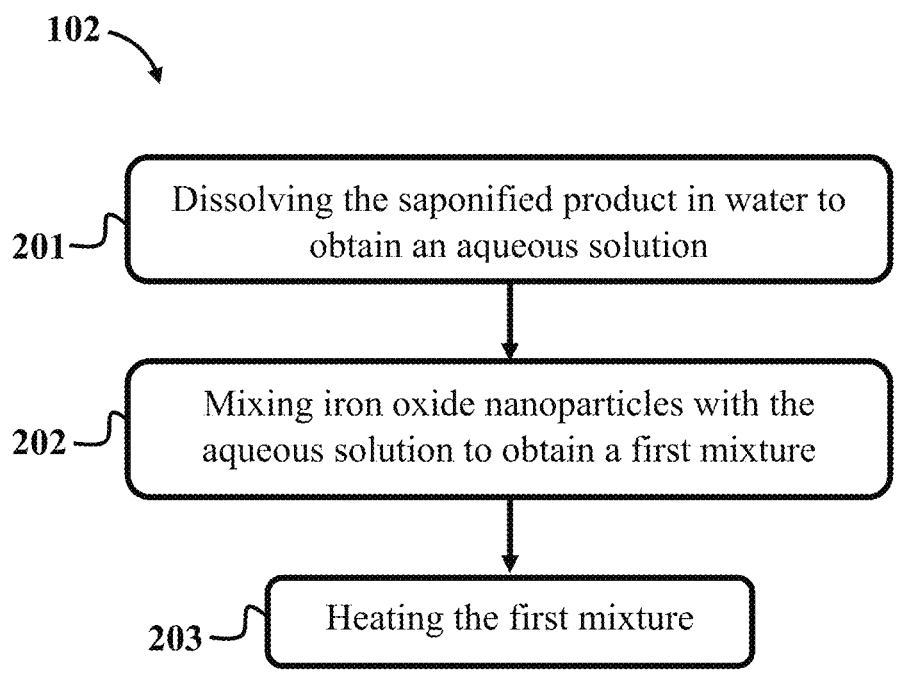
FIG. 2 illustrates an implementation of a step of adsorbing fatty acids of a seed oil on surfaces of iron oxide nanoparticles.

FIG. 2 illustrates an implementation of the step 102 (labeled in FIG. 1) of adsorbing the fatty acids of the seed oil on surfaces of iron oxide nanoparticles to obtain iron oxide nanoparticles coated with fatty acids. Referring to FIG. 2, the step 102 may include a step 201 of dissolving the saponified product in water to obtain an aqueous solution; a step 202 of mixing iron oxide nanoparticles with the aqueous solution to obtain a first mixture; and a step 203 of heating the first mixture.

Referring to FIG. 2, according to one or more implementations, the step 201 of dissolving the saponified product in water to obtain an aqueous solution may include dissolving the saponified product in a predetermined volume of distilled water to obtain an aqueous solution with a concentration between 0.023 mmol/mL and 0.34 mmol/mL.

Referring to FIG. 2, according to one or more implementations, the step 202 of mixing iron oxide nanoparticles with the aqueous solution to obtain a first mixture may include mixing the iron oxide nanoparticles with the aqueous solution with a molar ratio of aqueous solution to iron oxide nanoparticles of between 0.3 mol/mol and 1.9 mol/mol. In an example, pH of the first mixture may be adjusted at approximately 9.5.

Referring to FIG. 2, according to one or more implementations, the step 203 of heating the first mixture may include placing the first mixture in an oven with a temperature of between 100° C. and 195° C. for 30 min to 6.5 hours. The fatty acids in the saponified product may be adsorbed on surfaces of the iron oxide nanoparticles during the step 203 of heating the first mixture and iron oxide nanoparticles coated with fatty acids may be obtained.

Referring back to FIG. 1, according to one or more implementations, the step 103 of washing the iron oxide nanoparticles coated with fatty acids with a polar solvent to obtain a third mixture may include washing the iron oxide nanoparticles coated with fatty acids with a polar solvent such as acetone. The polar phase, for example the acetone phase, may include tocopherol, sterol, tocotrienols, and squalene.

Referring to FIG. 1, according to one or more implementations, the step 104 of separating the iron oxide nanoparticles coated with fatty acids from the third mixture by a magnet may include subjecting the third mixture to a magnetic force thereby attracting and separating the iron oxide nanoparticles coated with fatty acids from the third mixture.

Referring to FIG. 1, according to one or more implementations, the step 105 of mixing the polar phase with a non-polar solvent and distilled water to obtain a two-phase solution may include mixing the polar phase with ethanol, hexane, and distilled water. In an implementation, the polar phase may be mixed with ethanol, hexane, and distilled water in a two-phase separator. The temperature of the two-phase separator may be controlled by, for example, a water bath at a temperature between 10° C. and 40° C. Squalene is a non-polar compound and has a tendency towards being dissolved in the non-polar organic solvent of hexane. The non-polar phase may further be separated by the two-phase separator in the step 106. In an implementation, the separated non-polar phase may be dried in the step 107 to obtain squalene.

EXAMPLE 1

In this example, iron oxide ($Fe_3O_4$) magnetic nanoparticles were synthesized by a co-precipitation method. Ferrous chloride ($FeCl_2$) and ferric chloride ($FeCl_3$) with a mol ratio of 2/1 ($FeCl_2/FeCl_3$) were mixed in water at a temperature of 40° C. and a pH of 11. Then, the solution was mixed with a magnetic stirrer at 800 rpm for 30 min. Finally, synthesized iron oxide nanoparticles were washed with distilled water (3-4 times) and were separated using a magnetic force.

For the saponification reaction, 5 g of a sample seed oil, pumpkin seed oil in this example, was added to a container and then 50 ml of an ethanolic KOH solution was added to the sample seed oil, and the obtained mixture was placed in a thermal reflux at a temperature of approximately 80° C. for 1 h. Esters, triglycerides and free fatty acids react with potassium hydroxide and are converted to soap under the thermal reflux. Then, the mixture was placed in an oven at a temperature of 70-80° C. until it was fully dried and all the ethanol solvent was removed.

After saponification reaction, 2.86 mmol of the saponified product was completely dissolved in 61 mL of distilled water and then poured into a container containing 5.2 mmoles of the synthesized iron oxide nanoparticles at a pH of 9.5. The container was placed in an oven at 132° C. for 3.75 h to dry the synthesized iron oxide nanoparticles. The fatty acids were adsorbed on the synthesized iron oxide nanoparticles during the drying process due to evaporation of water from the solution.

Figure 3A:
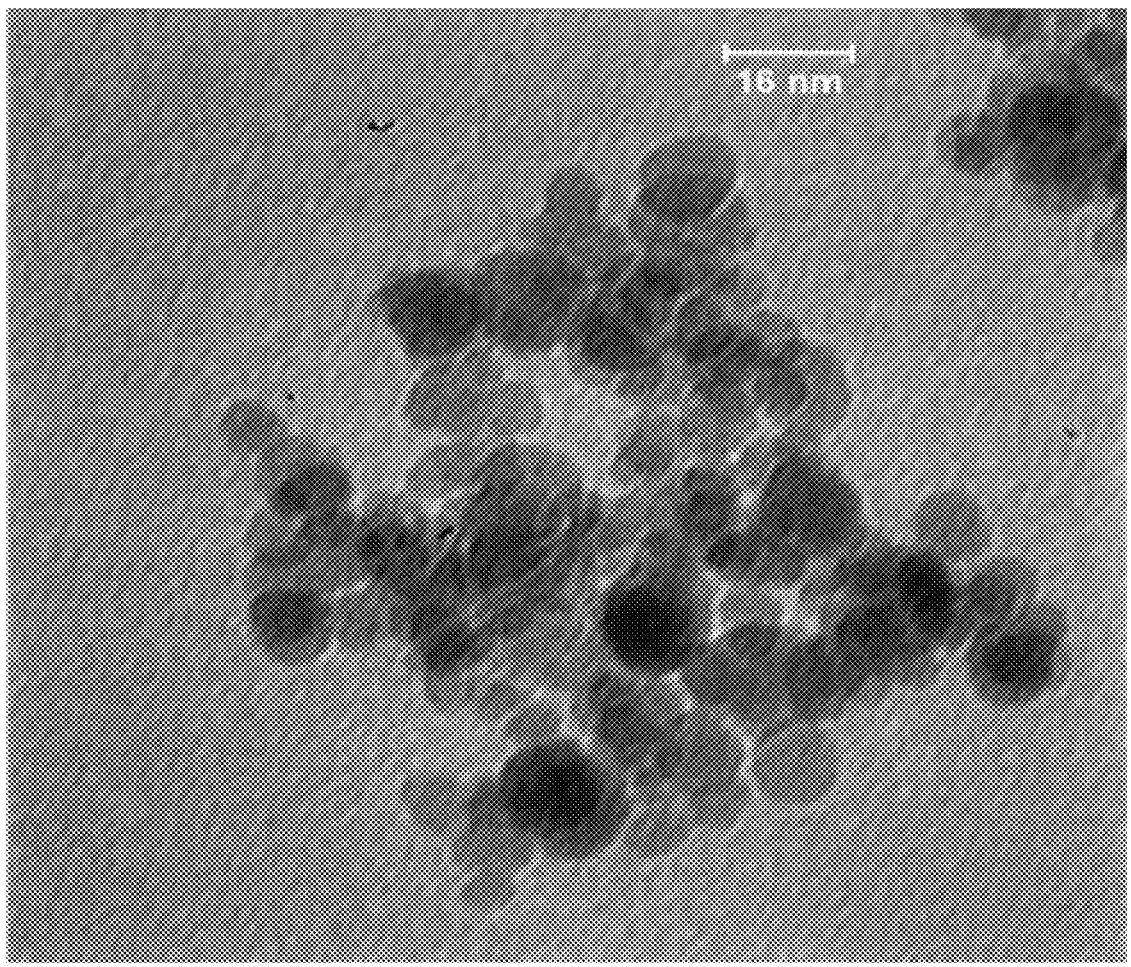
FIG. 3A is a transmission electron microscope (TEM) image of iron oxide nanoparticles before being coated with fatty acids, according to an implementation of the present disclosure.
Figure 3B:
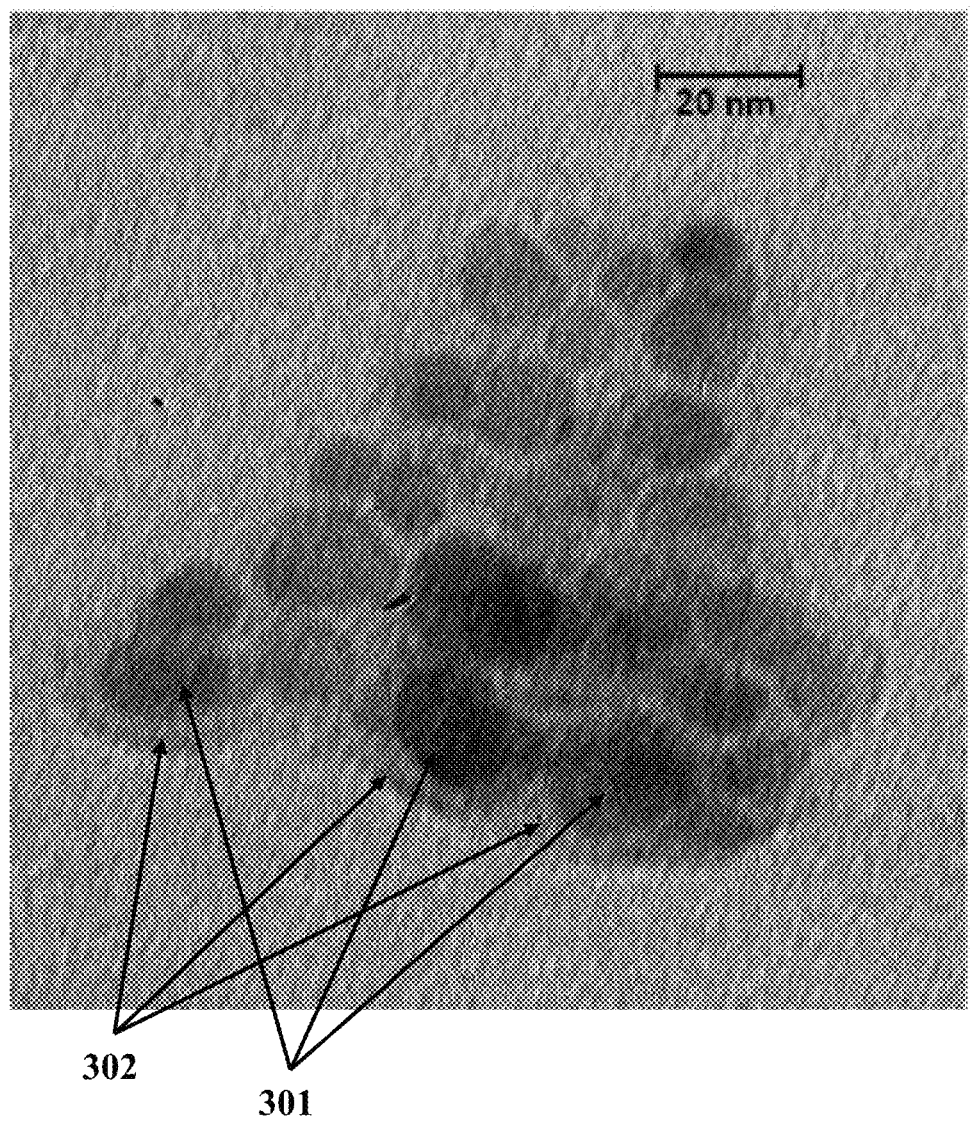
FIG. 3B is a TEM image of iron oxide nanoparticles after being coated with fatty acids, according to an implementation of the present disclosure.

FIG. 3A is a transmission electron microscope (TEM) image of iron oxide nanoparticles before being coated with fatty acids, according to an implementation of the present disclosure. FIG. 3B is a TEM image of iron oxide nanoparticles after being coated with fatty acids, according to an implementation of the present disclosure. Referring to FIG. 3B, darker spots 301 represent the iron oxide nanoparticles and lighter spots 302 around the darker spots 301 represent the fatty acid layers around the iron oxide nanoparticles which indicates a successful coating of the iron oxide nanoparticles with the fatty acids. Referring to FIGS. 3A and 3B, the average diameter of the iron oxide nanoparticles is approximately 10 nm, and the mean thickness of the fatty acid layers around the nanoparticles is approximately 5 nm.

After fatty acids were adsorbed on the synthesized iron oxide nanoparticles, the coated iron oxide nanoparticles were washed with 25 mL of an acetone solution. The coated iron oxide nanoparticles were separated from the mixture using a magnetic field.

Figure 4:
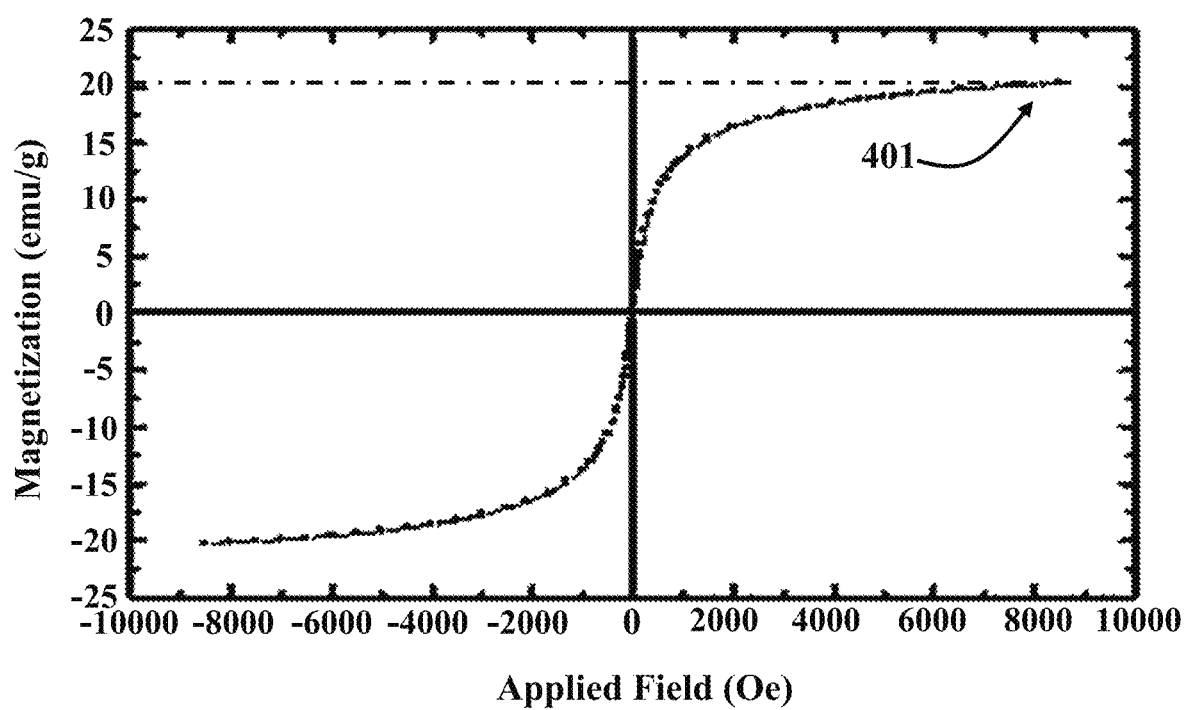
FIG. 4 illustrates a magnetization curve of coated iron oxide nanoparticles with fatty acids, according to an implementation of the present disclosure.

FIG. 4 illustrates a magnetization curve of the coated iron oxide nanoparticles with the fatty acids, according to an implementation of the present disclosure. Referring to FIG. 4, a magnetic saturation 401 of 20 emu/g is obtained for the coated nanoparticles, which indicates that coated nanoparticles possess super paramagnetic properties. In other words, the coated nanoparticles can be separated by a magnetic field.

Figure 5:
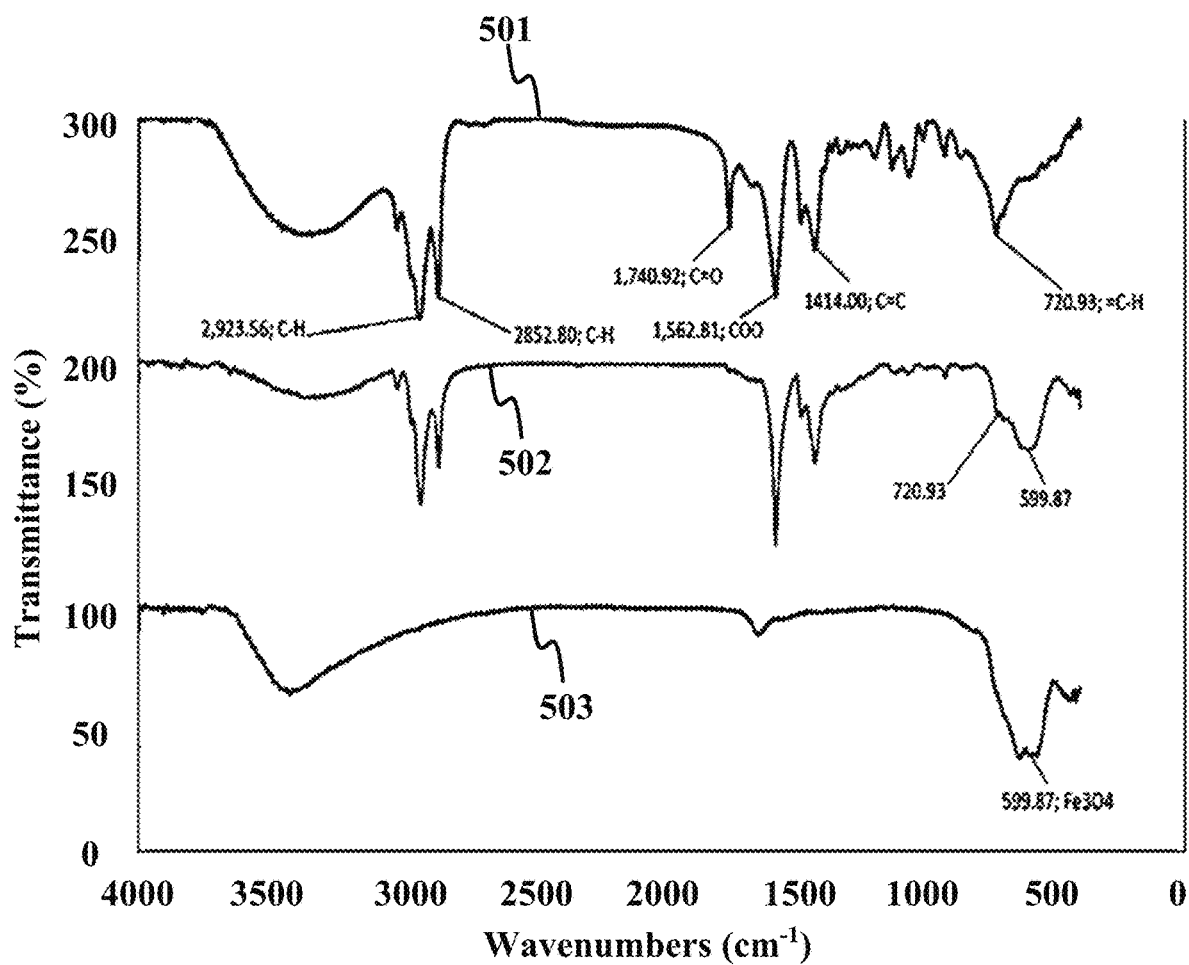
FIG. 5 illustrates Fourier transform infrared (FTIR) spectra of potassium soap of pumpkin seed oil, coated nanoparticles with fatty acids, and iron oxide nanoparticles, according to an implementation of the present disclosure.

FIG. 5 illustrates Fourier transform infrared (FTIR) spectra of potassium soap of pumpkin seed oil (referred to herein as saponified product) (spectrum 501), coated nanoparticles with fatty acids (spectrum 502), and iron oxide nanoparticles (spectrum 503), coated nanoparticles with fatty acids (spectrum 502). Referring to FIG. 5, the band COO— at 1,562 $cm^{-1}$ in the spectrum (502) indicates that the fatty acids are successfully attached to the iron oxide nanoparticles as carboxylate functional groups. The carboxylate functional groups are key factors that ensure a smooth adsorption of the fatty acids on the magnetic iron oxide nanoparticles. Referring to spectrum 501, the bands at 2923 and 2852 $cm^{-1}$ were attributed to C—H stretching modes. Referring to spectrum 502, the bands at 2923 and 2852 $cm^{-1}$ are still present after the nanoparticles are coated with the fatty acids. Furthermore the depth of these peaks at 2923 and 2852 $cm^{-1}$ remains the same in both spectra 501 and 502, which suggests that the saponification reaction did not have any effect on the content of unsaturated fatty acids and saponification reaction could be used for separation of unsaturated compounds, such as squalene in seed oils.

After separation of the coated iron oxide nanoparticles from the mixture by the magnetic field, the remaining solvent is an un-saponifiable phase which contains tocopherol, sterol and tocotrienols along with squalene and a trace amount of the fatty acids. The remaining solvent was then mixed with 20 ml of ethanol, 20 ml of hexane and 50 ml of distilled water to isolate squalene from other components. The operation was performed in a two-phase separator. By shaking the two-phase separator, a turbulent condition was created in the separator and two phases, an organic and an aqueous phase, were separated. Squalene is non-polar compound and has a tendency to be dissolved in a non-polar solvent, such as hexane. After extraction, hexane was separated and dried under argon and extracted mass was determined for a certain amount of 1.6 g oil. This extraction procedure was repeated at various temperatures as 10, 20, 25, 30 and 40° C.

Figure 6:
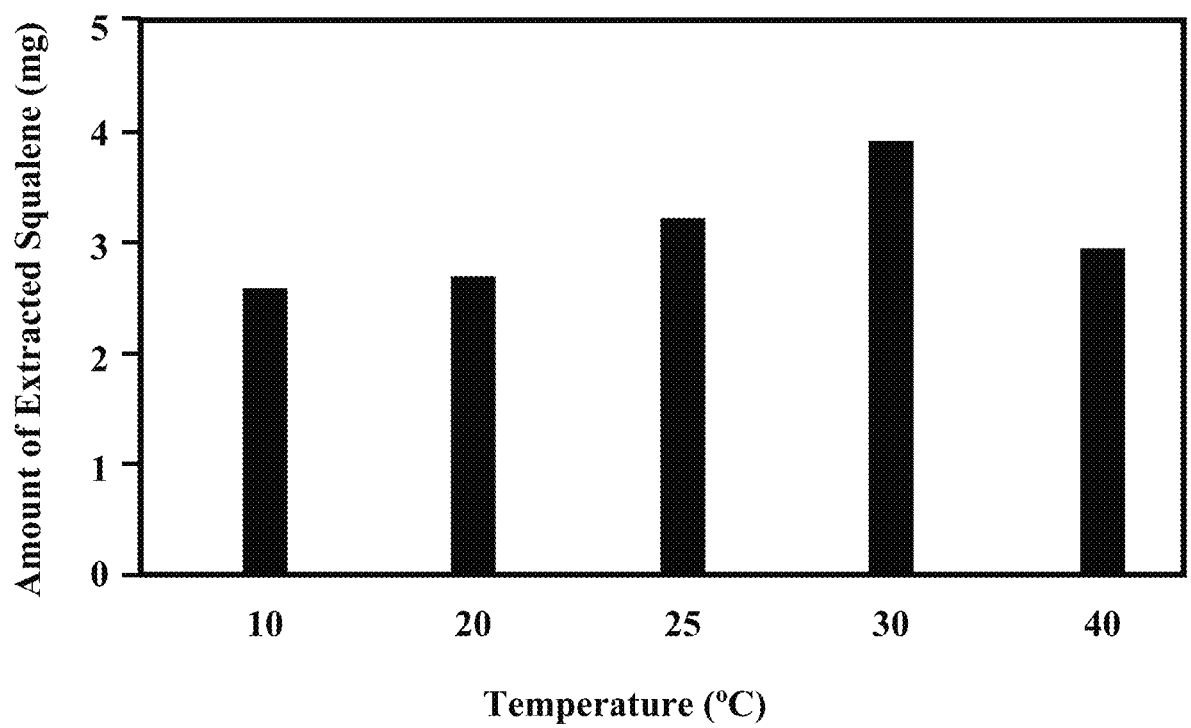
FIG. 6 is a graph that illustrates amounts of squalene extracted from 1.6 g of a pumpkin seed oil at different extraction temperatures, according to one or more implementations of the present disclosure.

FIG. 6 illustrates amounts of squalene extracted from 1.6 g of a pumpkin seed oil at different extraction temperatures, according to one or more implementations of the present disclosure. Referring to FIG. 6, the amount of extracted squalene increases with increasing extraction temperature from 10° C. to 30° C. Further increase in the extraction temperature from 30° C. to 40° C. decreases the amount of extracted squalene.

EXAMPLE 2

In this example, the anti-angiogenic potential of the extracted squalene is evaluated in an in-vivo angiogenesis study utilizing chorioallantoic membrane of chicken eggs (CAM) as the model for this study. To this end, 60 chicken eggs were separated into four groups. The groups included a witness group labeled as G1, a group treated with a base treatment solution of sorbitan trioleate and polysorbate 80 with a ratio of 1:1 labeled as G2, a group treated with a base treatment solution containing squalene with a concentration of 10 µg/ml of the base treatment solution labeled as G3, and a group treated with a base treatment solution containing squalene with a concentration of 20 µg/ml of the base treatment solution labeled as G4.

The four group of eggs as described above were placed in a hatchery device with an automatic rotation at a condition of 38° C. and relative humidity of 57%. After 1 day of incubation, a laminar hood was used to remove a part of each egg's crust and then using sterile paraffin a window is created on each egg. After 5 days of incubation, CAM formation starts in the eggs and after 8 days extends beyond half of the internal volume of each egg. Vascular treatment was performed at the 8th day. To this end, the windows on the eggs were removed and a gelatin sponge containing albumin, agar solution in normal saline, and 200 µl penicillin-streptomycin, was placed on each egg's CAM. 10 µl of the squalene solution was poured on the sponges with a specific concentrations mentioned for each of the four groups. Then, the windows were covered again and the eggs were returned to the incubator.

Figure 7A:
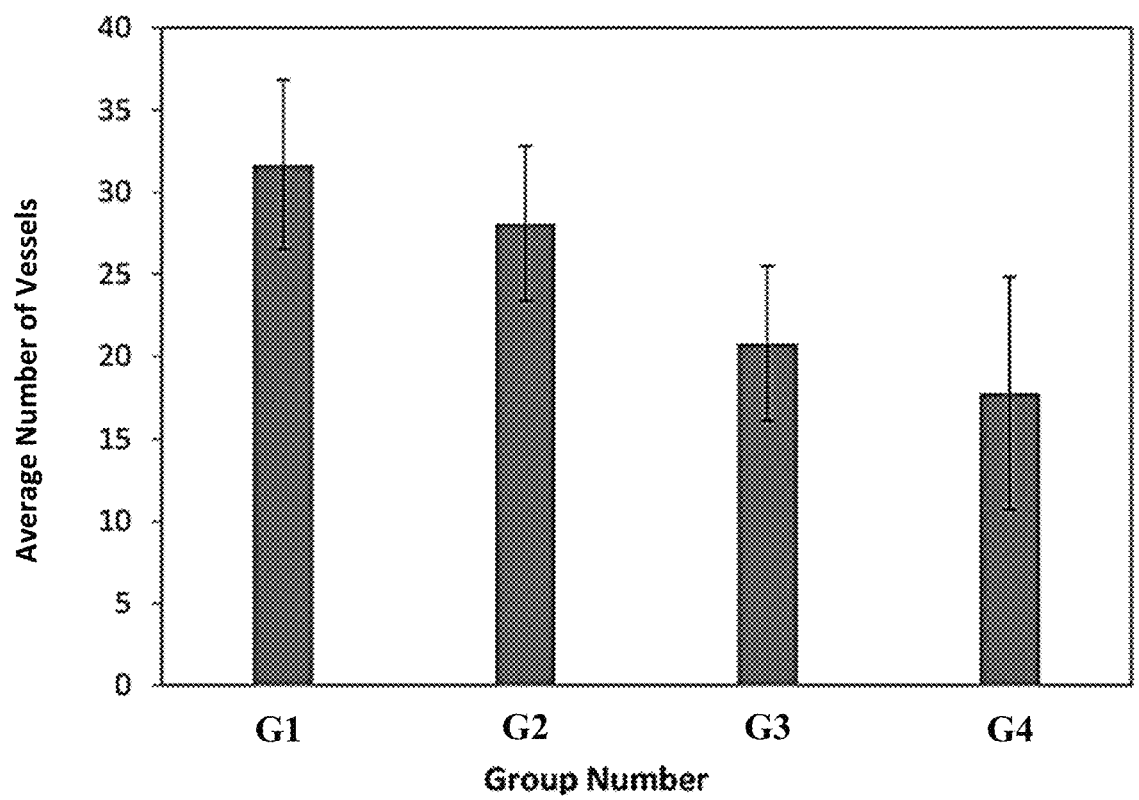
FIG. 7A is a graph that illustrates average numbers of blood vessels measured in 12th day of incubation in areas of eggs covered by sponges for four groups of G1, G2, G3, and G4, according to an implementation of the present disclosure.
Figure 7B:
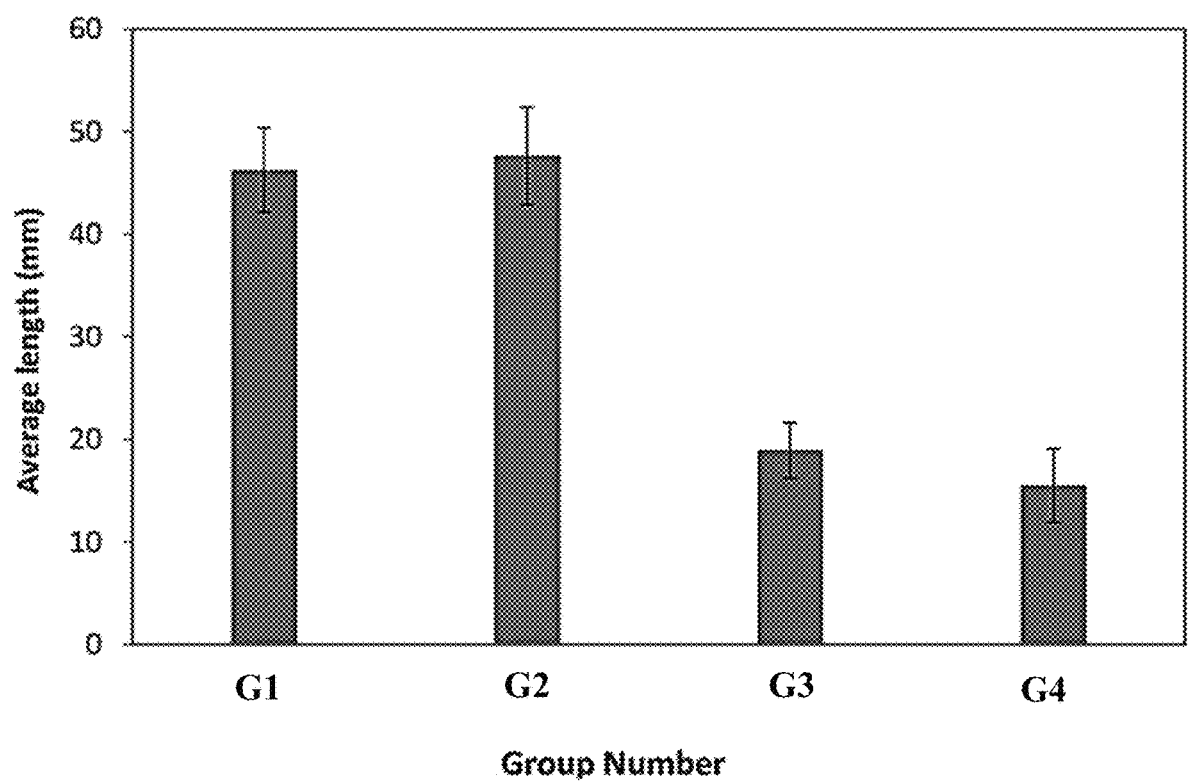
FIG. 7B is a graph that illustrates average lengths of blood vessels measured in $12^{th}$ day of incubation in areas of the eggs covered by the sponges for the four groups of G1, G2, G3, and G4, according to an implementation of the present disclosure.

FIG. 7A illustrates average numbers of blood vessels measured in $12^{th}$ day of incubation in areas of the eggs covered by the sponges for the four groups of G1, G2, G3, and G4. FIG. 7B illustrates average lengths of blood vessels measured in $12^{th}$ day of incubation in areas of the eggs covered by the sponges for the four groups of G1, G2, G3, and G4. Referring to FIGS. 7A and 7B, there is not any meaningful difference between the average number and length of the blood vessels in groups G1 and G2. By comparing the average and length of the blood vessels in groups G3 and G4, it may be observed that fewer blood vessels are formed under the areas covered by the sponges containing squalene. The difference between the number and length of the vessels formed in groups G3 and G4 indicates that anti-angiogenic property of squalene is dose-dependent.

While the foregoing has described what are considered to be the best mode and/or other examples, it is understood that various modifications may be made therein and that subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study, except where specific meanings have otherwise been set forth herein. Relational terms such as "first" and "second" and the like may be used solely to distinguish one entity or action from another without necessarily requiring or implying any actual such relationship or order between such entities or actions. The terms "comprises," "comprising," or any other variation thereof, as used herein and in the appended claims are intended to cover a non-exclusive inclusion, encompassing a process, method, article, or apparatus that comprises a list of elements that does not include only those elements but may include other elements not expressly listed to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is not intended to be used to interpret or limit the scope or meaning of the claims. In addition, in the foregoing Detailed Description, it can be seen that various features are grouped together in various implementations. Such grouping is for purposes of streamlining this disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into this Detailed Description, with each claim standing on its own as a separately claimed subject matter.

While various implementations have been described, the description is intended to be exemplary, rather than limiting and it will be apparent to those of ordinary skill in the art that many more implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for squalene extraction from a seed oil, the method comprising:
    subjecting the seed oil to a saponification reaction to obtain a saponified product;
    dissolving the saponified product in water to obtain an aqueous solution;
    mixing iron oxide nanoparticles with the aqueous solution to obtain a first mixture;
    heating the first mixture to obtain iron oxide nanoparticles coated with fatty acids;
    washing the iron oxide nanoparticles coated with fatty acids with a polar solvent to obtain a third mixture, the third mixture including a polar phase and the iron oxide nanoparticles coated with fatty acids;
    separating the iron oxide nanoparticles coated with fatty acids from the third mixture by a magnetic field to obtain the polar phase;
    mixing the polar phase with a non-polar solvent and distilled water to obtain a two-phase solution, the two-phase solution including a non-polar phase and an aqueous phase;
    separating the non-polar phase; and
    drying the separated non-polar phase to obtain squalene.

2. The method according to claim 1, wherein the saponification reaction includes:
    mixing the seed oil with an ethanolic KOH solution to obtain a second mixture; and
    heating the second mixture under reflux to obtain the saponified product.

3. The method according to claim 2, wherein heating the second mixture under reflux includes heating the second mixture at a temperature of between 70° C. and 80° C.

4. The method according to claim 1, wherein the aqueous solution has a concentration of between 0.023 mmol/mL and 0.34 mmol/mL.

5. The method according to claim 1, wherein heating the first mixture includes heating the first mixture at a temperature of between 100° C. and 195° C.

6. The method according to claim 5, wherein heating the first mixture at a temperature of between 100° C. and 195° C. is carried out for 30 min to 6.5 hours.

7. The method according to claim 1, wherein mixing iron oxide nanoparticles with the aqueous solution to obtain a first mixture includes mixing iron oxide nanoparticles with the aqueous solution with a molar ratio of aqueous solution to iron oxide nanoparticles of between 0.3 and 1.9.

8. The method according to claim 1, wherein the polar solvent includes acetone.

9. The method according to claim 1, wherein the organic solvent is hexane.

10. The method according to claim 1, wherein mixing the second remaining solution with an organic solvent and distilled water to obtain a two-phase solution is carried out at a temperature of between 10° C. and 40° C.

* * * * *